US00PP23396P2

(12) United States Plant Patent
Olesen

(10) Patent No.: US PP23,396 P2
(45) Date of Patent: Feb. 19, 2013

(54) MINIATURE ROSE PLANT NAMED 'POULPAR068'

(50) Latin Name: ***Rosa* hybrid**
Varietal Denomination: Poulpar068

(75) Inventor: Mogens Nyegaard Olesen, Fredensborg (DK)

(73) Assignee: Poulsen Rose A/S, Fredensborg (DK)

( * ) Notice: Subject to any disclaimer, the term of this patent is extended or adjusted under 35 U.S.C. 154(b) by 0 days.

(21) Appl. No.: 13/507,009

(22) Filed: May 31, 2012

(51) Int. Cl.
*A01H 5/00* (2006.01)

(52) U.S. Cl. ..... Plt./117

(58) Field of Classification Search ..... Plt./117
See application file for complete search history.

*Primary Examiner* — June Hwu
*Assistant Examiner* — Louanne Krawczewicz Myers

(57) ABSTRACT

A new miniature rose plant that has abundant, white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar068'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpar068', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar068' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar068' was selected by the inventor as a single plant from the progeny of the hybridization in 2006.

Asexual reproduction of 'Poulpar068' by cuttings was first done by Mogens N. Olesen in the nursery in Fredensborg, Denmark in 2007. This initial and other subsequent propagations conducted in controlled environments have demonstrated that the characteristics of 'Poulpar068' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar068', exhibited in plants that are 3 months of age. Specifically illustrated in the drawing are flowers at various stages of development, flower in parts, leaves, and stems.

DETAILED DESCRIPTION OF THE VARIETY

The following is a description of 'Poulpar068', as observed in its growth in glasshouses in Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra015', U.S. Plant Pat. No. 14,309 are compared to 'Poulpar068' in Chart 1.

CHART 1

| | 'Poulpar068' | 'Poulra015' |
|---|---|---|
| Petalage: | 35 petals, 5 of which are petaloids. | 13 to 15 petals under normal conditions with 0 to 3 petaloids. |
| Flower Diameter: | 60 to 65 mm | 55 mm |
| General Tonality of Flower Color: | White Group 155A | Yellow Group 11D |

FLOWER AND FLOWER BUD

Blooming habit: Continuous.

Flower bud:

*Size*.—Upon opening, 20 mm in length from base of receptacle to end of bud. 10 mm in diameter.

*Bud form*.—

*Bud color*.—As sepals unfold, petals are White Group 155A.

*Sepals*.—Upper Surface: Color: Green Group 138A. Texture: Smooth, moderately pubescent. Lower Surface: Color: Yellow Green Group 144A. Texture: Smooth. Shape: Apex: Cirrhose. Base: Flat at union with receptacle. Margins: Margins have moderate foliaceous appendages on three of the five sepals. Size: 30 to 35 mm long by 7 mm wide.

*Receptacle*.—Surface Texture: Smooth. Shape: Funnel shaped. Size: 6 mm tall and 9 mm wide. Color: Yellow Green Group 144A.

*Pedicel*.—Surface: Smooth. Length: 15 to 25 mm. Diameter: Generally 3 mm. Color: Yellow-Green Group 144A. Strength: Strong.

*Borne*.—Singly.

Flower bloom:

*Fragrance*.—Light floral scent.

*Duration*.—As a pot plant, flowers last up to 28 days.

*Size*.—Flower diameter is 60 to 65 mm when open. Flower depth is 20 mm.

*Form*.—General shape is a hybrid tea with a high pointed center.

*Shape of flower, side view*.—Upon opening, the upper portion is flat. The lower portion is flat.

Petalage: Under normal conditions, flowers have 35 petals total, 5 of which are petaloids.

Color:

*General tonality*.—On open flower White Group 155A. There are no changes to the flower color as the blooms mature.

*Upon opening, petals*.—Outermost and innermost petals are White Group 155A on the upper and lower surface. No other coloration observed at the petal base.

*After opening, petals*.—Outermost and innermost petals are White Group 155A on the upper and lower surface. No other coloration observed at the petal base.

Petals:

*Petal reflex*.—Strong.

*Margin*.—Entire, uniform, with moderate undulations.

*Shape*.—Generally broad and elliptic. Apex shape: Rounded. Base shape: Acute.

*Size*.—30 mm (l) by 30 mm (w). Innermost petals are 20 mm (l) by 12 mm (w).

*Texture*.—Smooth.

*Thickness*.—Above average.

Petaloids:

*Quantity*.—5 on average.

*Shape*.—Irregular, and asymmetric. The apex and base are acute.

*Color*.—White Group 155A.

*Size*.—20 mm (l) by 10 mm (w).

Reproductive organs:

*Pollen*.—None Observed.

*Anthers*.—Size: 2 mm long. Color: Greyed-Yellow Group 160B. Quantity: 45 on average.

*Filaments*.—Color: Yellow Group 2B. Length: About 3 mm.

*Pistils*.—Length: About 3 mm long. Quantity: 20 on average.

*Stigmas*.—Level relative to the length of the filaments and the height of the anthers. Color: Red Group 43C.

*Styles*.—Color: Greyed-Yellow Group 160C.

*Seed formation*.—Not observed.

PLANT

Plant growth: Upright. Plants are 17 cm in height on average, and 15 cm wide.

Stems:

*Color*.—Juvenile growth: Yellow-Green Group 144A. Mature growth: Green Group 138A.

*Length*.—Canes are 12 to 15 cm from the base of the plant to the flowering portion.

*Diameter*.—About 4 mm.

*Internodes*.—On mature canes, there is an average distance of 13 mm between nodes.

*Surface texture*.—Young and mature wood is smooth.

Prickles:

*Incidence*.—No long prickles observed.

Plant foliage: Normal number of leaflets on normal leaves in middle of the stem: 5 to 7 leaflets.

*Compound leaf size*.—80 mm (l) by 60 mm (w).

*Quantity*.—8 leaves per 10 cm of stem.

*Color of juvenile foliage*.—Upper Leaf Surface: Yellow-Green Group 146A. Lower Leaf Surface: Yellow-Green Group 146B. Anthocyanin: At the leaflet margins, Greyed-Purple Group 183A.

*Color of mature foliage*.—Upper Leaf Surface: Yellow-Green Group 147A. Lower Leaf Surface: Yellow-Green Group 147B.

Plant leaves and leaflets:

*Stipules*.—Size: About 4 mm in length. 2 to 3 mm wide. Shape: Linear, slightly broad based with outward extending apices. Margins: Finely serrated with few stipitate glands. Color: Yellow-Green Group 146A. Quantity: 2 stipules per leaf.

*Petiole*.—Length: 20 mm on average. Diameter: About 2 mm. Upper surface: Yellow-Green Group 147A with intonations of Greyed-Purple Group 183A. Smooth. Lower surface: Yellow-Green Group 146B.

*Rachis*.—Length: 20 mm on average. Diameter: About 2 mm. Upper surface: Yellow-Green Group 147A with intonations of Greyed-Purple Group 183A. Smooth. Lower surface: Yellow-Green Group 146B.

*Leaflet*.—Size: 40 mm in length by 20 mm wide. Margin: Serrate. General Shape: Ovate. Apex Shape: Acute. Base Shape: Round. Texture: Smooth. Arrangement: Odd pinnate. Venation: Reticulate. Leaf Gloss: Somewhat glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: For a variety of the miniature class, the variety exhibits superior resistance to all forms of black spot and mildew.

What is claimed is:

1. A new and distinct variety of rose plant of the miniature class named 'Poulpar068', substantially as illustrated and described herein, due to its abundant, white flowers, vigorous growth, compact habit, suitability for production from softwood cuttings in pots, and durable flowers and foliage that make the variety suitable for distribution in the floral industry.

* * * * *

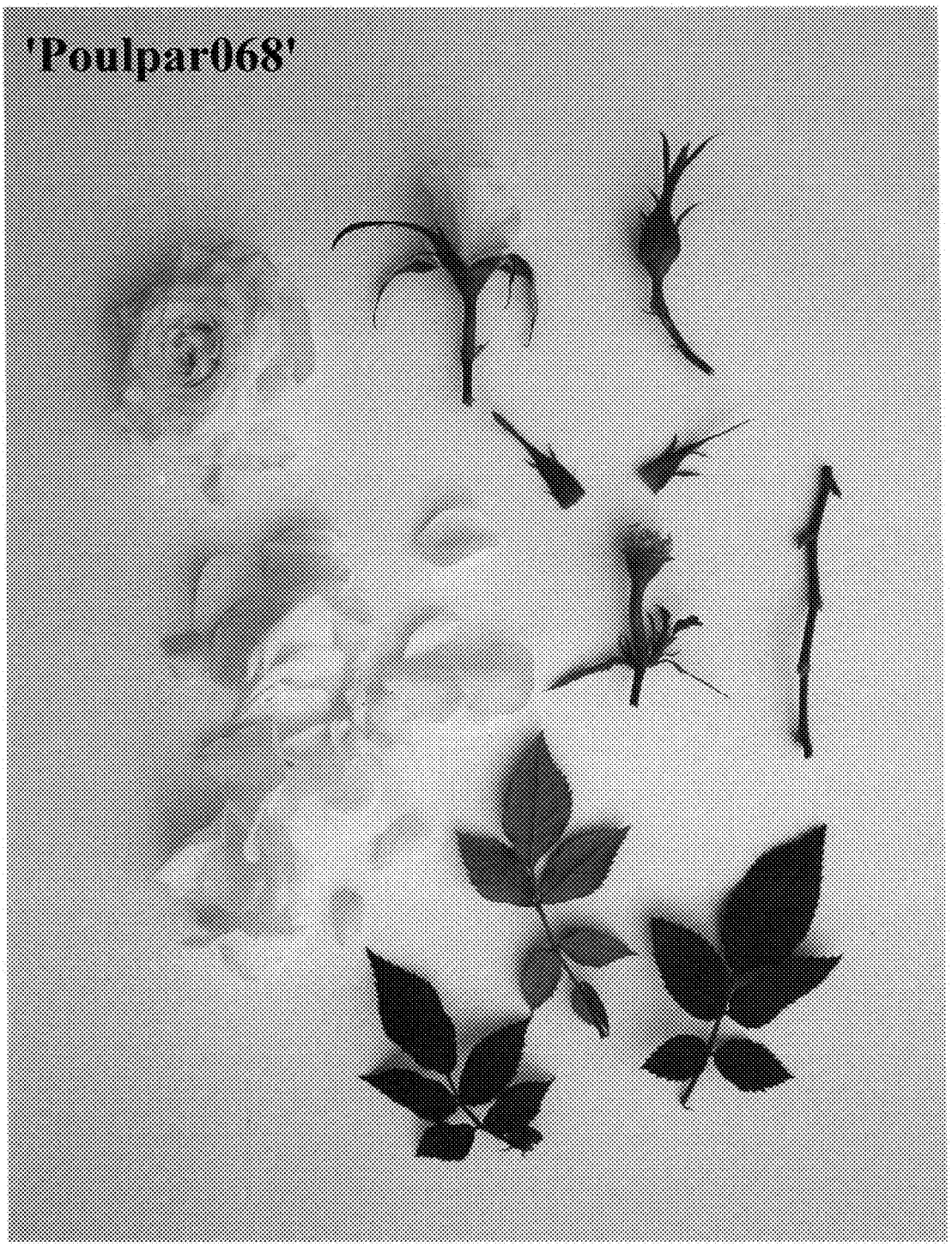
'Poulpar068'